United States Patent
Narayanan et al.

(10) Patent No.: US 11,087,883 B1
(45) Date of Patent: Aug. 10, 2021

(54) SYSTEMS AND METHODS FOR TRANSFER-TO-TRANSFER LEARNING-BASED TRAINING OF A MACHINE LEARNING MODEL FOR DETECTING MEDICAL CONDITIONS

(71) Applicant: Blue Eye Soft, Inc., Greer, SC (US)

(72) Inventors: Barath Narayanan, Dayton, OH (US); Russell Hardie, Dayton, OH (US); Vignesh Krishnaraja, Dayton, OH (US); Srikanth Kodeboyina, Greer, SC (US)

(73) Assignee: Blue Eye Soft, Inc., Greer, SC (US)

( * ) Notice: Subject to any disclaimer, the term of this patent is extended or adjusted under 35 U.S.C. 154(b) by 0 days.

(21) Appl. No.: 17/218,997

(22) Filed: Mar. 31, 2021

Related U.S. Application Data

(60) Provisional application No. 63/139,278, filed on Jan. 19, 2021, provisional application No. 63/004,268, filed on Apr. 2, 2020.

(51) Int. Cl.
*G16H 50/20* (2018.01)
*G06N 20/00* (2019.01)
(Continued)

(52) U.S. Cl.
CPC .............. *G16H 50/20* (2018.01); *G06K 9/627* (2013.01); *G06K 9/6256* (2013.01); *G06N 3/08* (2013.01);
(Continued)

(58) Field of Classification Search
CPC .......... G06N 3/08; G06N 20/00; G16H 30/20; G16H 50/20; G16H 50/70; G06T 7/0012;
(Continued)

(56) References Cited

U.S. PATENT DOCUMENTS 10,474,926 B1 * 11/2019 Dirac .................... G06K 9/6227
11,030,747 B1 * 6/2021 Feng ........................ G06T 15/08
(Continued)

OTHER PUBLICATIONS

Arias-Londoño et al. "Artificial Intelligence applied to chest X-Ray images for the automatic detection of COVID-19. A thoughtful evaluation approach." IEEE Access (Dec. 2020). (Year: 2020).*
(Continued)

*Primary Examiner* — Katrina R Fujita
(74) *Attorney, Agent, or Firm* — Padowithz Alce; Alce PLLC

(57) ABSTRACT

Systems and methods for transfer-to-transfer training using an imbalanced training dataset include reconfiguring an imbalanced training data corpus to a plurality of distinct class-balanced mini-corpora of training data, wherein the reconfiguring includes: (i) partitioning the imbalanced training data corpus into a plurality of mini-corpora of training data samples in which each distinct mini-corpus of the plurality of mini-corpora includes an entirety of the training data samples within the second subset of training data samples; and (ii) allocating an equal number of the training data samples of the first subset into each of the plurality of mini-corpora of training data samples; and transfer-to-transfer learning-based training a subject machine learning algorithm to a trained machine learning model based on implementing the transfer-to-transfer learning-based training using the plurality of distinct class-balanced mini-corpora, wherein in use, the trained machine learning model predicts a presence or a non-presence of COVID-19 based on image data.

17 Claims, 3 Drawing Sheets

(51) Int. Cl.
*G16H 50/70* (2018.01)
*G06K 9/62* (2006.01)
*G06N 3/08* (2006.01)
*G06T 7/00* (2017.01)
*G06T 7/11* (2017.01)
*G16H 30/20* (2018.01)

(52) U.S. Cl.
CPC .......... *G06N 20/00* (2019.01); *G06T 7/0012* (2013.01); *G06T 7/11* (2017.01); *G16H 30/20* (2018.01); *G16H 50/70* (2018.01); *G06T 2207/30061* (2013.01)

(58) Field of Classification Search
CPC ............ G06T 7/11; G06T 2207/30061; G06K 9/6256; G06K 9/627
See application file for complete search history.

(56) References Cited

U.S. PATENT DOCUMENTS

| | | | |
|---|---|---|---|
| 2016/0224892 A1* | 8/2016 | Sawada | G06N 3/08 |
| 2017/0024641 A1* | 1/2017 | Wierzynski | G06K 9/4628 |
| 2017/0337464 A1* | 11/2017 | Rabinowitz | G06F 17/16 |
| 2018/0144465 A1* | 5/2018 | Hsieh | G06N 3/08 |
| 2018/0144466 A1* | 5/2018 | Hsieh | G06T 7/0012 |
| 2018/0314975 A1* | 11/2018 | Zang | G06N 20/00 |
| 2018/0349633 A1* | 12/2018 | Takimoto | G06K 9/6215 |
| 2019/0102658 A1* | 4/2019 | Wang | G06K 9/6268 |
| 2019/0122077 A1* | 4/2019 | Tsishkou | G06K 9/629 |
| 2019/0122360 A1* | 4/2019 | Zhang | G06K 9/6267 |
| 2019/0156484 A1* | 5/2019 | Nye | G16H 50/20 |
| 2019/0180145 A1* | 6/2019 | Chen | G06K 9/6262 |
| 2019/0197139 A1* | 6/2019 | Yang | G06N 20/00 |
| 2019/0205620 A1* | 7/2019 | Yi | G06K 9/00268 |
| 2020/0012923 A1* | 1/2020 | Ghosh | G06K 9/00369 |
| 2020/0081980 A1* | 3/2020 | Eisenberg | G06F 16/35 |

OTHER PUBLICATIONS

Horry et al. "COVID-19 detection through transfer learning using multimodal imaging data." IEEE Access 8 (Aug. 2020): 149808-149824. (Year: 2020).*

Horry et al. "X-ray image based COVID-19 detection using pre-trained deep learning models." (Apr. 2020). (Year: 2020).*

Iqbal et al. "A Hybrid VDV Model for Automatic Diagnosis of Pneumothorax using Class-Imbalanced Chest X-rays Dataset." arXiv preprint arXiv:2012.11911 (Dec. 2020). (Year: 2020).*

Karthikeyan et al. "Transfer learning for decision support in Covid-19 detection from a few images in big data." 2020 IEEE International Conference on Big Data (Big Data). IEEE, Dec. 2020. (Year: 2020).*

Luz et al. "Towards an effective and efficient deep learning model for COVID-19 patterns detection in X-ray images." arXiv preprint arXiv:2004.05717 (Jul. 2020). (Year: 2020).*

Narayanan et al. "Transfer-to-Transfer Learning Approach for Computer Aided Detection of COVID-19 in Chest Radiographs." AI 1.4 (Nov. 2020): 539-557. (Year: 2020).*

Ozsahin et al. "Review on diagnosis of COVID-19 from chest CT images using artificial intelligence." Computational and Mathematical Methods in Medicine 2020 (Sep. 2020). (Year: 2020).*

Pereira et al. "COVID-19 identification in chest X-ray images on flat and hierarchical classification scenarios." Computer Methods and Programs in Biomedicine 194 (May 2020): 105532. (Year: 2020).*

Punn et al "Automated diagnosis of COVID-19 with limited posteroanterior chest X-ray images using fine-tuned deep neural networks." Applied Intelligence (Oct. 2020): 1-14. (Year: 2020).*

* cited by examiner

SYSTEMS AND METHODS FOR TRANSFER-TO-TRANSFER LEARNING-BASED TRAINING OF A MACHINE LEARNING MODEL FOR DETECTING MEDICAL CONDITIONS

CROSS-REFERENCE TO RELATED APPLICATIONS

This application claims the benefit of U.S. Provisional Application No. 63/139,278, filed 19 Jan. 2021, and U.S. Provisional Application No. 63/004,268, filed 2 Apr. 2020, which are incorporated herein in their entireties by this reference.

TECHNICAL FIELD(S)

This invention relates generally to the machine learning and artificially intelligent medical system fields, and more specifically to a new and useful system and method for intelligently curating training data and training machine learning models of a machine learning-based medical system in the machine learning and artificially intelligent medical system fields.

BACKGROUND

Artificial Intelligence (AI) is currently one of the fastest-growing technological fields. Referring to the simulation of human intelligence in machines through programming, AI is serving in many different fields such as medical, automobile, etc. Specifically, in the medical field, AI may be characterized as the scientific discipline pertaining to research studies, projects and applications which may help support decision-based medical tasks through knowledge and/or data-intensive computer-based solutions.

Currently, several diagnostic testing methods are being used to detect novel diseases (e.g., COVID-19) in the medical imaging field, including but not limited to, the Reverse-Transcription-Polymerase Chain Reaction (RT-PCR), Computed Tomography (CT), X-Ray, and the like. While these methods for detection may offer high specificity and accuracy in specified diseases, the world may be in need of a more widely available and rapid solution to assist doctors in identifying such disease.

While there may currently exist some technologies and/or techniques that attempt to detect novel diseases or other medical imaging complications, these existing technologies and/or technique implementations may not sufficiently detect such novel diseases with the use of medical imaging with accuracy and efficacy to provide an opportunity to those in all parts of the world. Additionally, these existing technologies and/or technique implementations lack the capabilities to detect new and/or recently encountered diseases due to a lack in availability of sample data which may cause a class imbalance problem, particularly, as it relates to requirements for an effective training corpus for training machine learning models for detecting novel diseases.

Therefore, there is a need in the medical field and machine learning field for systems and methods that enable intelligent techniques for diagnosing, detecting, and/or identifying specified attributes of graphical medical images. The embodiments of the present application described herein provide technical solutions that address, at least, the need described above, as well as the deficiencies of the state of the art described throughout the present application.

BRIEF SUMMARY OF THE INVENTION(S)

In one embodiment, a machine-learning based method for detecting covid-19 based on a transfer-to-transfer learning optimized training of a machine learning algorithm using an initially imbalanced training data corpus includes evaluating an imbalanced training data corpus of training data samples, comprising at least a first subset of training data samples with a first classification label and a second subset of training data samples with a second classification label; identifying that the first subset of training data samples includes a number of training data samples satisfying or exceeding a training corpus imbalance threshold, the first subset of training data samples having the number of training data samples greater than a number of training data samples within the second subset of training data samples; configuring the imbalanced training data corpus to a plurality of distinct class-balanced mini-corpora of training data samples, wherein the configuring includes: (i) partitioning the imbalanced training data corpus into a plurality of mini-corpora of training data samples in which each distinct mini-corpus of the plurality of mini-corpora includes an entirety of the training data samples within the second subset of training data samples; and (ii) allocating an equal number of the training data samples of the first subset into each of the plurality of mini-corpora of training data samples; and training a machine learning algorithm to a trained machine learning model based on the plurality of mini-corpora, wherein in use the trained machine learning model predicts a presence or a non-presence of covid-19 based on image data.

In one embodiment, the method includes randomly sampling the training data samples of the second subset to create the duplicated training data samples after allocating an entirety of the training data samples of the second subset.

In one embodiment, the first subset of training data samples comprises a plurality of distinct non-covid-19 image data samples.

In one embodiment, the second subset of training data samples comprises a plurality of distinct covid-19 image data samples.

In one embodiment, the machine learning model comprises a convolution neural network.

In one embodiment, implementing an image segmentation of each of the training data samples of the imbalanced training data corpus, wherein the training data samples comprise a plurality of distinct human thoracic images, wherein the image segmentation includes: partitioning each of the plurality of distinct human thoracic images to two or more distinct, non-overlapping parts.

In one embodiment, the plurality of distinct human thoracic images comprises a plurality of distinct chest radiographs of human lungs having covid-19 and a plurality of distinct chest radiographs of human lung not having covid-19.

In one embodiment, the pre-processing includes normalizing each of the training data samples of the imbalanced training data corpus by adjusting a contrast between a plurality of distinct components within each of the plurality of distinct human thoracic images.

In one embodiment, the randomly selected training data samples selected from the second subset for inclusion are non-repetitive with respect to the training data samples from the second subset already present in a given mini-corpus of the plurality of mini-corpora of training data samples.

In one embodiment, training the machine learning algorithm includes: providing only a first one of the plurality of mini-corpora of training data samples as input training data examples to the machine learning algorithm during a first training phase.

In one embodiment, the method includes collecting a corpus of learned weights from the trained machine learning; and transferring the corpus of learned weights to a new iteration of the machine learning algorithm.

In one embodiment, the method includes training the new iteration of the machine learning algorithm including: providing only a second one of the plurality of mini-corpora of training data samples as input training data examples to the new iteration of the machine learning algorithm during a subsequent training phase.

In one embodiment, the method includes transferring each corpus of learned weights of the machine learning algorithm during each distinct training phase to a subsequent iteration of the machine learning algorithm for training with a distinct one of the plurality of mini-corpora of training data samples until each of the plurality of mini-corpora of training data samples has been using in a distinct training phase.

In one embodiment, a method for training a machine learning algorithm for detecting covid-19 based on a transfer learning optimized imbalanced training data corpus, includes evaluating an imbalanced training data corpus of training data samples, comprising at least a first subset of training data samples with a first classification label and a second subset of training data samples with a second classification label; identifying that the first subset of training data samples includes a number of training data samples satisfying or exceeding a training corpus imbalance threshold, the first subset of training data samples having the number of training data samples greater than a number of training data samples than the second subset of training data samples; partitioning the imbalanced training data corpus into a plurality of mini-corpora of training data samples having an equal number of training data samples, wherein the partitioning includes: (i) allocating an equal number of the training data samples of the first subset into each of the plurality of mini-corpora; (ii) allocating a number of the training data samples of the second subset into each of the plurality of mini-corpora; and (iii) recycling a subset of the training data samples of the second subset and allocating the recycled training data samples into the plurality of mini-corpora until the number of the training data samples of the first subset matches the training data samples of the second subset within each of the plurality of mini-corpora; training a machine learning algorithm to a trained machine learning model based on the plurality of mini-corpora, wherein in use the trained machine learning model predicts a presence or a non-presence of covid-19 based on image data.

In one embodiment, a machine learning-based Computer-Aided-Detection (CAD) system for detecting covid-19 based on a transfer-to-transfer learning optimized training of a machine learning algorithm using an initially imbalanced training data corpus, includes a machine learning-based Computer-Aided-Detection system implemented by one or more computers and that includes: a training data reconfiguration module that: evaluates an imbalanced training data corpus of training data samples, comprising at least a first subset of training data samples with a first classification label and a second subset of training data samples with a second classification label; identifies that the first subset of training data samples includes a number of training data samples satisfying or exceeding a training corpus imbalance threshold, the first subset of training data samples having the number of training data samples greater than a number of training data samples within the second subset of training data samples; configures the imbalanced training data corpus to a plurality of distinct class-balanced mini-corpora of training data samples, wherein the configuring includes: (i) partitioning the imbalanced training data corpus into a plurality of mini-corpora of training data samples in which each distinct mini-corpus of the plurality of mini-corpora includes an entirety of the training data samples within the second subset of training data samples; and (ii) allocating an equal number of the training data samples of the first subset into each of the plurality of mini-corpora of training data samples; and a machine learning algorithm training module that: trains a machine learning algorithm to a trained machine learning model based on the plurality of mini-corpora, wherein in use the trained machine learning model predicts a presence or a non-presence of covid-19 based on image data.

In one embodiment, the machine learning-based CAD system includes an image segmentation module that: segments of each of the training data samples of the imbalanced training data corpus, wherein the training data samples comprise a plurality of distinct human thoracic images, wherein the image segmentation includes: partitions each of the plurality of distinct human thoracic images to two or more distinct, non-overlapping parts.

DESCRIPTION OF THE PREFERRED EMBODIMENTS

The following description of the preferred embodiments of the present application are not intended to limit the inventions to these preferred embodiments, but rather to enable any person skilled in the art to make and use these inventions.

Overview

The embodiments of the present application provide an intelligent diagnosis technique that is capable of identifying and/or detecting specified diseases within a specified region of a human corpus with the use of visual representations, such as an image. Using one or more trained (deep) machine learning models, the embodiments of the present application may function to identify, detect, and/or diagnose any variety of visual representation input provided to the system. The one or more (deep) machine learning models, post deployment, can continue to train using unknown and previously incomprehensible data samples and/or medical images. As a result, the underlying system that implements the (deep) machine learning models may function to evolve with increasing interactions with medical professionals and training rather than being governed by a fixed set of predetermined rules for identifying, detecting, and/or diagnosing defined disease parameters, as may be accomplished in the current state of the art.

The intelligent diagnosis technique of the present application employs a robust ensemble of machine learning models and related systems that operate to ingest the great number of medical image diagnosis performed. Accordingly, using these finely tuned and perpetually evolving and tunable machine learning models, a system implementing the several embodiments of the present application can predict specified diseases with high accuracy and, in some embodiments, in real-time (e.g., as the event is occurring or shortly thereafter) compute a diagnosis score for each input visual representation that is received by the system.

1. System for Computer Aided Image Processing and Detection

Figure 1:
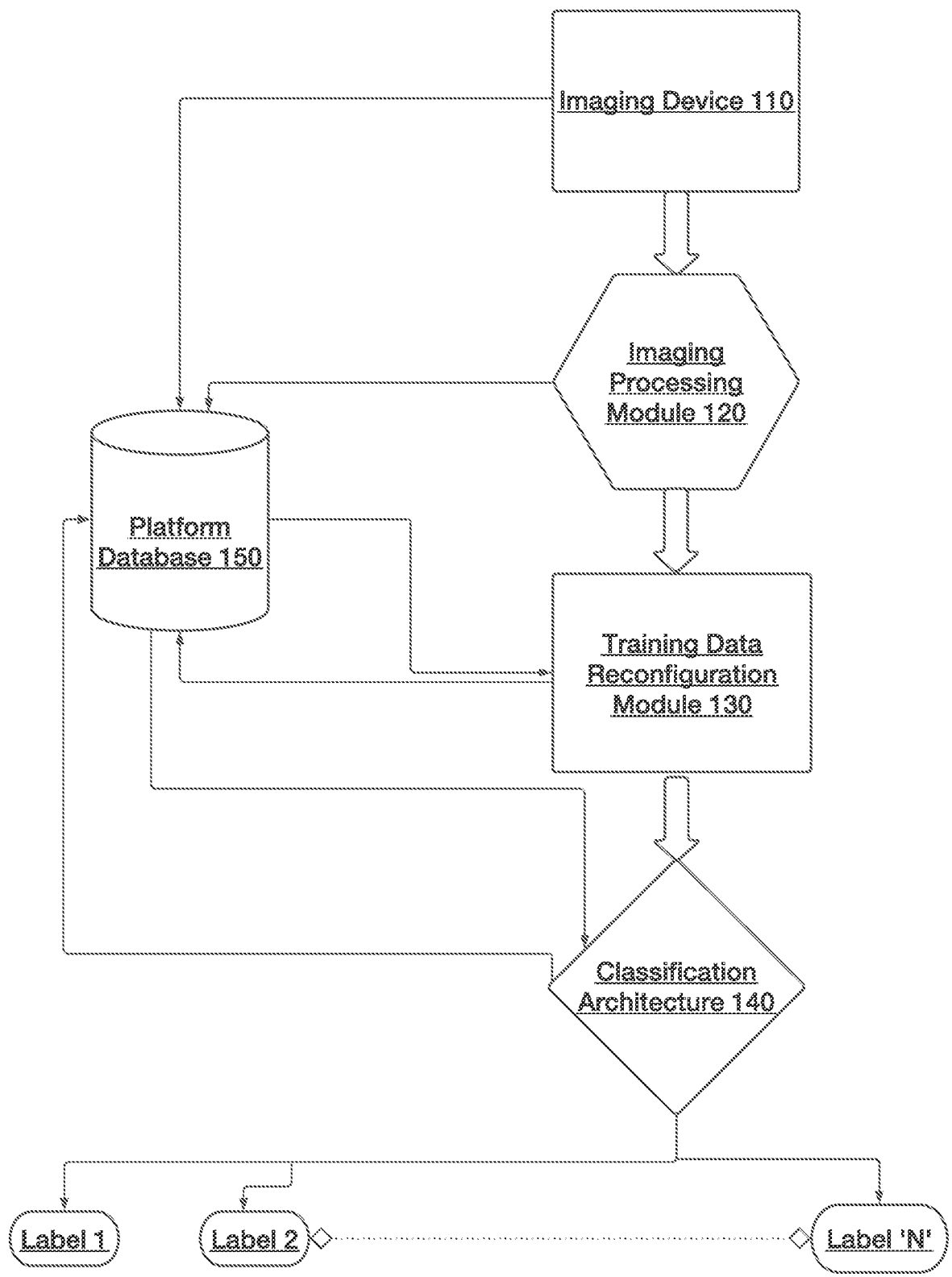
FIG. 1 illustrates a schematic representation of a system in accordance with one or more embodiments of the present application.

As shown in FIG. 1, a system 100 for classifying data by detecting a target attribute in graphical data that may include, an imaging device 110, an image processing module 120, a training data reconfiguration module 130, a machine learning module 140, and a platform database 150.

The imaging device 110 may function to capture one or more images of at least one section of a human corpus. In one or more embodiments, the imaging device may capture imaging data in any form, including, but not limited to, radiographs, X-ray based techniques (e.g., fluoroscopy, mammography, angiogram and/or the like), Computed Tomography (CT) scans etc. Additionally, or alternatively, the imaging device may include a device, such as a camera, that may function to capture a 2D photograph and/or a 3D graphical image of one or more organs/parts of a human corpus. In some embodiments, the imaging device 110 may function to capture an image of an image. That is, the imaging device 110 may be a device capable of capturing a secondary, tertiary, or subsequent image of an original or other image to thereby create an enhanced image and/or an image that may be suitable for one or more tasks including training a machine learning model.

The image processing module 120 may function to pre-process and segment training data samples of a training data corpus, wherein the preprocessing may include, but is not limited to, enhancing contrast; thresholding data (e.g., removing pixels that may be brighter or darker than a threshold value); removing bias (e.g., removing annotation labels); converting imaging data to another visual form (e.g., converting images to greyscale); reshaping or resizing imaging data (e.g., cropping images), and the segmenting may include, but is not limited to, partitioning each of a plurality of distinct data samples (e.g., images) into two or more distinct, non-overlapping parts.

The training data reconfiguration module 130 may function to evaluate an imbalanced training data corpus of training data samples, wherein the imbalanced training data set may comprise at least a first subset of training data samples with a first classification label and a second subset of training data samples with a second classification label. In some embodiments, the training data reconfiguration module 130 may function to identify that the first subset of training data samples may include a number of training data samples satisfying or exceeding a training data corpus imbalance threshold, the first subset of training data samples having a number of training data samples greater than a number of training data samples within a second subset of training data samples; configure the imbalanced training data corpus to a plurality of distinct class balanced mini corpora of training data samples, wherein the configuring may include partitioning the imbalanced training data corpus into a plurality of mini corpora of training data samples in which each distinct mini corpus of the plurality of mini corpora may include an entirety of the training data samples within the second subset of training data samples and allocating an equal number of the training data samples of the first subset into each of the plurality of mini corpora of training data samples.

The machine learning module 140 may function to train a machine learning algorithm to a trained machine learning model that may be used to predict a presence or absence of a target disease (e.g., COVID-19) using one or more model inputs (e.g., features of radiograph images or the like).

The platform database 150 may function to collect and store any or all values generated by the system 100 including, but not limited to, one or more training data sets, parameters and hyperparameters for learning and/or outputs of predictions made by a machine learning model. In one or more embodiments, the platform database 150 may enable a continuous retrieval of data for a training process.

It shall be noted that sub-systems and components of the system 100 may be connected or placed in operable communication using any suitable network and in any suitable manner. For instance, components of the system 100 may be directly connected over a network, wherein, the network may include any public (e.g., the internet) or private network (e.g., the intranet), a virtual private network, a global area network, a cellular network, any combination of the aforementioned and the like.

Figure 2:
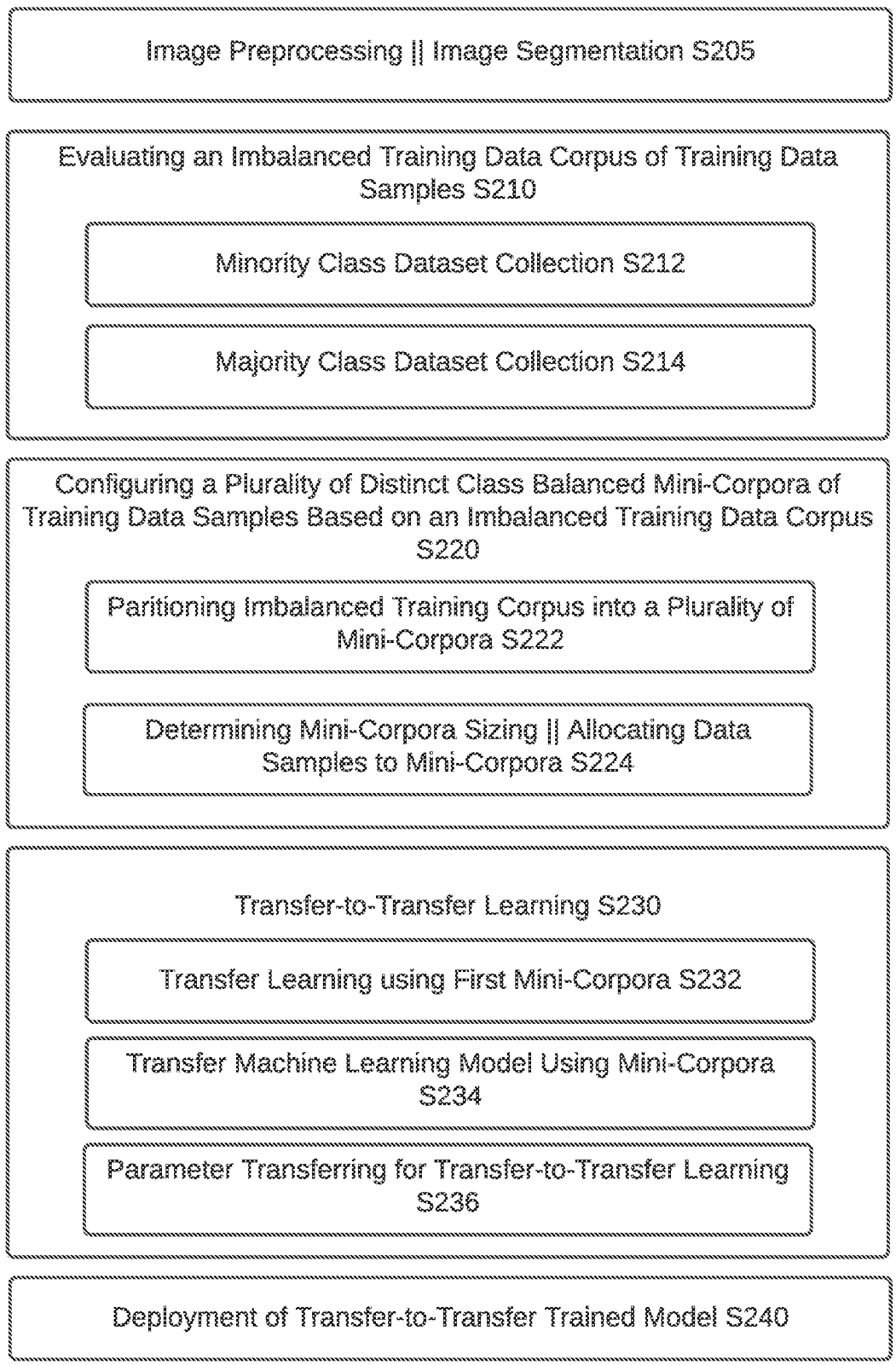
FIG. 2 illustrates an example method in accordance with one or more embodiments of the present application.

2. Method for Intelligently Configuring Class-Balanced Training Corpora and Method for a Transfer-To-Transfer Learning-Based Training of a Machine Learning Model Used in Computer Aided Detection As shown in FIG. 2, the method 200 for configuring a class-balanced training corpora and implementing a machine learning-based transfer-to-transfer learning includes evaluating an imbalanced training data corpus of training data samples S210, configuring an imbalanced training data corpus to a plurality of distinct class-balanced mini-corpora of training data samples S220, implementing a transfer-to-transfer learning of a machine learning model S230, and deploying a trained transfer-to-transfer trained machine learning model S240.

2.05 Image Preprocessing||Image Segmentation

Optionally, S200 may include S205, which includes an image preprocessing and/or image segmentation of any given data samples of a training corpus, may function to include an image preprocessing and/or segmentation module that may function to segment the training data samples of the imbalanced training data corpus. In one or more embodiments, the preprocessing may include, but is not limited to, enhancing contrast; thresholding data (e.g., removing pixels that may be brighter or darker than a threshold value); removing bias (e.g., removing annotation labels); converting graphical data to another visual form (e.g., converting images to greyscale); reshaping or resizing graphical data (e.g., cropping images); and/or the like. Additionally, or alternatively, the segmentation of the visual representations may include, but is not limited to partitioning each of a plurality of distinct data samples into two or more distinct, non-overlapping parts.

2.10 Evaluating an Imbalanced Training Data Corpus of Training Data Samples

S210, which includes evaluating an imbalanced training data corpus of training data samples, may function to identify and/or collect a corpus of training data having two or more distinct classes of training data samples, such as a minority-class and a majority-class, and evaluate the corpus of training data to identify an optimal class-balancing configuration.

2.12 Minority Class Dataset Collection

S210 includes S212, which includes selecting and/or collecting data corpus for a minority class, may function to identify minority class sample data based on a search and selection of the minority class sample data from a corpus of samples having the specified minority class attributes. In a preferred embodiment, all data sample images for a minority class may be from the same area of a human corpus. In such preferred embodiments, both minority class and majority class data sample images may display the same area of a human corpus. In one or more embodiments, S212 may identify and/or collect a plurality of data sample images of a specified medical condition which may be labeled as a minority class of an imbalanced training data corpus. In such embodiments, each sample image may be pre-identified to assure the images contain the necessary attributes required contained in the sample image to display the specified medical condition. Additionally, or alternatively, in such embodiments, the selected sample images may be one or more of a specified form of visual representation, such as a radiograph, CT scan, x-ray, and/or the like.

For example, in the case of where COVID-19 is selected as the minority classification, although limited in data samples, all available data sample images that are identified with a COVID-19 classification label in images of lungs of a human corpus are collected and labeled as the minority class. In such case, chest radiographs may be a selected choice in imaging technique as it may be distinctly identifiable as COVID-19 to radiologist.

2.14 Majority Class Dataset Collection

S210 includes S214, which includes selecting and/or collecting data corpus for a majority class, may function to identify majority class sample data based on a search and selection of the majority class sample data from a corpus of samples having the specified majority class attributes. In a preferred embodiment, all data sample images for a majority class may be from the same area of a human corpus. In such preferred embodiments, both minority class and majority class data sample images may display the same area of a human corpus. Additionally, or alternatively, in one or more embodiments, each sample image may be preidentified to assure that the images contain distinct differing attributes from the minority class displaying a differing medical condition or the like.

For example, in the case mentioned in S212, where COVID-19 may be identified as the minority classification, sample images without the COVID-19 classification obtained from the same area of the human corpus may be collected and labeled as the majority class. In such cases, other medical conditions such as, pneumonia, tuberculosis, lung cancer, healthy, and the like, may also be collected as a majority class sample images. In one or more embodiments, including such other medical conditions within the majority class dataset may have technical benefits including, but not limited to, improving performance of a machine learning model to differentiate between images representing a target disease (e.g., COVID-19) other diseases (e.g., flu, pneumonia, and/or the like), and image samples without disease.

2.20 Configuring a Plurality of Distinct Class Balanced Mini-Corpora of Training Data Samples Based on an Imbalanced Training Data Corpus S220, which includes configuring an imbalanced training data corpus to a plurality of distinct class-balanced mini-corpora of training data samples, may function to create and/or generate a plurality of distinct mini-corpora based on specified aspects of an imbalanced corpus of data samples (e.g., number of data samples, size of the dataset, etc.).

2.22 Partitioning Imbalanced Training Corpus into a Plurality of Mini-Corpora S220 includes S222, which includes converting an imbalanced training data corpus to a plurality of distinct class-balanced mini-corpora of training data samples, may function to create a plurality of distinct mini-corpora based on a total number of data samples and/or minority data samples within the imbalanced training data corpus for creating each of a plurality of class-balanced mini-corpora. In one or more embodiments, S222 may function to identify a selected minority class containing a number of data samples below a specified threshold number (e.g., below a minimum number of data samples in a class) and/or threshold value that may result in an automated execution of a partitioning of the imbalanced training corpus for creating a plurality of mini-corpora from the imbalanced training data corpus. In such embodiment, the number of generated mini-corpora may be determined based on dividing the number of majority data sample images in the imbalanced training data corpus by the number of minority class data sample images in the imbalanced training data corpus.

For example, if there are 1000 majority class sample images and only 10 minority class images in the imbalanced training data corpus, the relative disparity and/or ratio between the minority class images and the majority class images may indicate a class imbalance within the imbalanced corpus of training data. In such example, to determine the number of mini-corpora generated in this case for creating class-balanced mini training data corpora, S222 may function to divide the 1000 majority class images by the 10 minority class images creating a total of 100 mini-corpora.

Additionally, or alternatively, in one or more variant embodiments, S222 includes a partitioning of a non-evenly divisible imbalanced data corpus. In such embodiments, the number of generated mini-corpora may be determined by dividing the number of majority data sample images to the number of minority class data sample images and the quotient number may be either rounded up or down to the nearest whole number, which may allow for one or more mini-corpora to differ in size to one another.

2.24 Determining Mini-Corpora Sizing||Allocating Data Samples to Mini-Corpora S220 includes S224, which includes determining a size and/or configuring data samples allocations for each distinct class-balanced mini-corpora, may function to create and/or allocate/spread data samples of a majority class of data samples and a minority class of data samples to each of the identified mini-corpora, as described in S222, thereby forcing a creation of a plurality of distinct class-balanced mini-corpora. In a preferred embodiment, the size of each distinct class-balanced mini-corpora may be double the total amount of minority class images of the imbalanced training data corpus. In such embodiment, S224 may function to each mini-corpora the entirety of the minority class of data sample images as well as an equal, or approximately equal, number of randomly sampled members of the majority class of data sample images which may create a singular class-balanced mini-corpora. It shall be recognized, that in such preferred embodiment, each mini-corpora may not contain a repetition of any majority class data sample images in any of the distinct mini-corpora generated thereby creating a plurality of mini corpora of training data samples in which the minority class of data samples may be entirely or substantially (e.g., 80%+ overlap or the like, etc.) the same and the majority class of data samples within each distinct mini corpora may have non-repeated samples and/or non-overlapping data samples between any two distinct mini corpora.

Additionally, or alternatively, in one or more variant implementations, S224 may function to utilize any subset of the minority class of data sample images for combinations of distinct mini-corpora to create a class-balance within each mini corpora. In such implementation, any individual mini-corpora may utilize any subset of the identified minority class data sample images which may result in differing mini-corpora sizes as well as an unequal amount of majority to minority class data sample images.

Additionally, or alternatively, in a further variant implementation, S224 may function to contain any combination of the majority class images including repetitions samples of the majority class, a use of subset of the majority class, and/or the like. In such implementation, any individual mini-corpora may utilize any subset of the identified majority class data sample images which may result in differing mini-corpora sizes having overlapping majority class samples among the mini-corpora.

It shall be recognized that in some embodiments, the method 200 or the like may function to implement any suitable combination of the above-described configuration parameters to create a class-balanced mini-corpora, and/or the like.

2.30 Transfer-To-Transfer Learning

Figure 3:
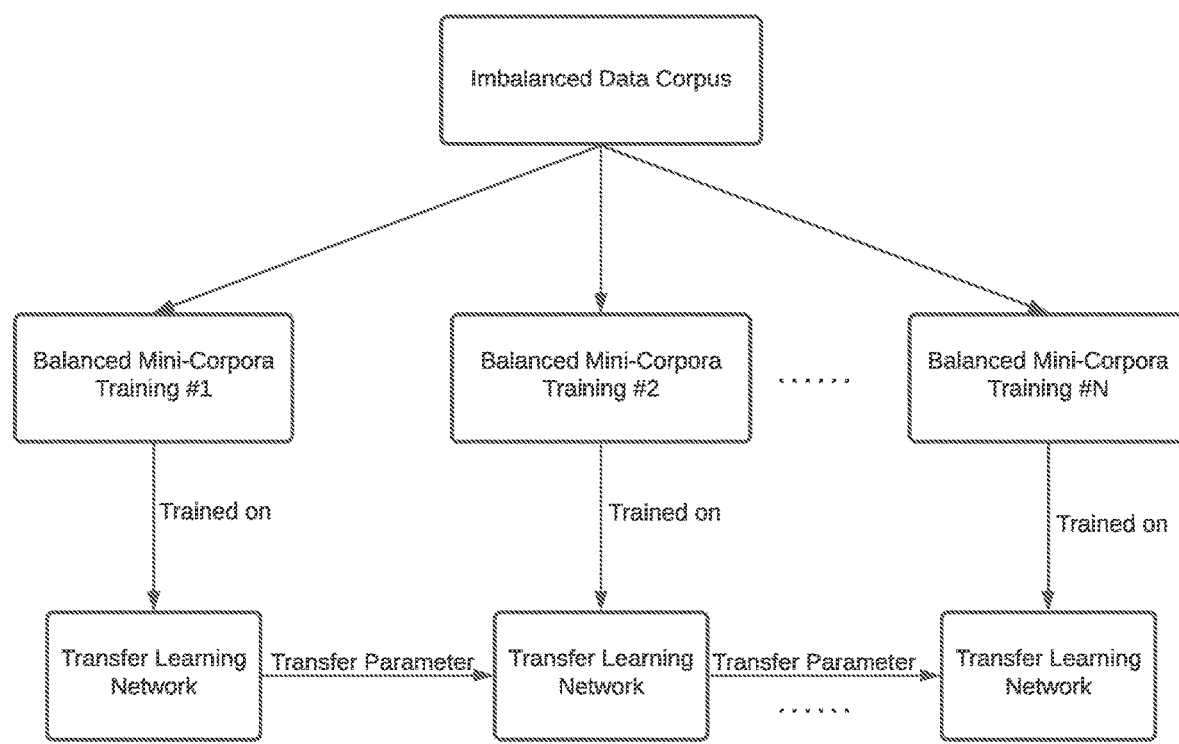
FIG. 3 illustrates an exemplary schematic for a transfer-to-transfer learning based on a forced balanced training corpora comprising a plurality of distinct mini corpora in accordance with one or more embodiments of the present application.

S230, which includes implementing an enhanced training of a machine learning model based on transfer-to-transfer learning, may function to iteratively train a target machine learning algorithm based on multiple sequential transfers of learned parameters (e.g., weights, biases, coefficients and/or the like) between one or more transferring machine learning models and the target machine learning algorithm (i.e., a transferee or recipient algorithm) using each of a plurality of distinct class-balanced mini corpora (derived in S220), as shown by way of example in FIG. 3.

In a first implementation, S230 may function to implement a transfer-to-transfer learning of a target machine learning algorithm using a previously trained machine learning model. In a second implementation, S230 may function to implement a transfer-to-transfer learning and training of a target machine learning algorithm by first training a base or untrained version of the target machine learning algorithm in a first training iteration and subsequently, initialize an iterative transfer-to-transfer learning-based training of the target machine learning model with the version of the target machine learning model algorithm trained in the first iteration.

In one or more embodiments, transfer learning may include training a base neural network or the like on a base training data set to perform a first machine learning task, then repurposing and/or transferring learned parameters of the neural network to a second target neural network to be trained on a target training data set and task. In one or more implementations, transfer learning may refer to a machine learning method where a model developed for a machine learning task may be used (fully or partially) as a starting point for developing a model for distinct machine learning task. For example, if a machine learning model may have been trained to predict whether an input image may contain cars; such a machine learning model may be used as a starting point to develop another machine learning model that may predict whether an input image may contain trucks. In one or more implementations, knowledge, in terms of learnable parameters, may be transferred from one model, that may have been trained with an effective corpus of labeled data, to a new model for which a lesser amount of labeled data may be available or for which faster training may be desired.

In one or more embodiments, transfer-to-transfer learning may refer to a machine learning method, that may use learned parameters of a previous or historical phase of training as starting values of learnable parameters for a next phase of training a machine learning model, wherein, a distinct phase of training a machine learning model, may be referred to, herein, as an epoch of training. In one or more implementations, each epoch of training a model may use a distinct set of training data corpus or a subset of training data corpus (mini-corpora). Additionally, or alternatively, in some implementations, different epochs of training may have different training hyperparameters, wherein, hyperparameters may refer to one or more parameters of a machine learning algorithm that may control or be set before the training process. Examples of algorithm hyperparameters may be learning rate, batch size and/or the like.

2.32 Transfer Learning Using a First Mini-Corpora

S230 includes S232, which includes implementing a transfer learning method for training a machine learning algorithm using a first mini-corpora, may function to develop or configure a new machine learning model by using learnable parameters (e.g., weights, coefficients, biases, and/or the like) of a pre-trained model as starting values of parameters for the new machine learning model, and starting a first epoch of training, by providing only a first one of a plurality of class-balanced mini-corpora of training data samples, as an input training data examples to the machine learning algorithm during the first training epoch.

In one or more embodiments, S232 may function to implement transfer-to-transfer learning for a first training epoch by transferring parameter values from a pre-trained model and updating the parameter values during a first epoch of training, using only a subset of a training data corpus, to generate parameter values that may be used for multiple iterations of transfer-to-transfer learning in subsequent epochs of training.

In one or more embodiments, S232 may function to utilize a pre-trained convolutional neural network (CNN) as a starting model, wherein, the pre-trained CNN may have been trained on a corpus (e.g., millions) of medical or non-medical images for transfer learning. In such embodiments, features of a CNN may be more generic in initial layers and more specific in latter layers towards a desired or new machine learning task based on a training of the latter layers of the CNN with a task-specific corpus of data (e.g., the class-balanced mini corpora of training data). For example, in image recognition cases, initial layers of a neural network may function to identify lines, regions, shapes and/or the like, whereas later layers may function to identify exact type of image.

For example, in one or more medical imaging applications, initial layers of a neural network may function to identify whether a test image may belong to a corpus of data set of human images; identify which organ and/or part of human corpus the test image may belong to and/or the like. Additionally, or alternatively, later layers may identify whether the test image may represent a healthy and/or diseased organ and/or part of human corpus; in such instances, if the test image may be identified as diseased, the later layers of a neural network may function to identify a type of disease that the diseased organ and/or part of human body may be suffering from.

In a preferred implementation, S232 may function to replace a last fully connected layer of a pre-trained neural network with one or more fully connected units and further training may be initiated to classify a data set (e.g., medical images) into two or more distinct classes. In one or more variant implementations, S232 may function to selectively retrain one or more layers of a pre-trained CNN, before using the pre-trained CNN for transfer learning, instead of replacing the one or more layers (terminal layers) of a CNN.

In additional and/or alternative, implementations, efficacy of a machine learning model for predicting a target disease (e.g., COVID 19) may be improved by implementing transfer learning using an initial CNN trained on other similar data sets and/or for other similar applications compared to using random weights initially.

2.34 Training a Machine Learning Model Using Mini-Corpora

S230 includes S234, which includes training a machine learning model using individual mini-corpora sequentially, may function to include computing values of one or more learnable parameters (e.g., weights, biases, coefficients and/or the like) of a machine learning model based on a (supervised) training of the machine learning model using each mini-corpora of training data samples.

In one or more embodiments, S234 may function to use a pre-trained model without modification for training, wherein the training may start with transfer learning using a first mini corpora in a first training epoch and transfer-to-transfer learning using each of a plurality of mini corpora of training data samples in later training epochs.

Additionally, or alternatively, S234 may function to integrate a pre-trained model into a new CNN for further training, wherein, further training may start with transfer learning using a first mini corpora and transfer-to-transfer learning using each of a plurality of mini corpora of training data samples. In a first implementation, one or more layers of a pre-trained CNN may be frozen or unchanged during training, such as its parameters (e.g., weights, coefficients, biases and/or the like) while only another part of the CNN may be subject to change based on a training using one or more of the plurality of distinct mini corpora of training data samples.

In a second implementation, one or more layers of a pre-trained part of a CNN may be fine-tuned during training, such as its parameters (e.g., weights, coefficients, biases and/or the like), belonging to layers of pre-trained part of CNN may be updated during training process. In this second implementation, S234 may function to restrict value of the weights, coefficients, and/or biases to within predetermined ranges. In a third implementation, one or more hyperparameters (e.g., learning rate and/or the like) may be configurable for one or more layers of a pre-trained part of CNN to achieve a balance between freezing and fine-tuning during training. In a fourth implementation, a pre-trained model may be used as a feature extractor and may function to pre-process training data to extract relevant features.

2.36 Parameter Transferring for Transferring-To-Transfer Learning

S230 includes S236, which includes implementing a transfer-to-transfer learning method for training a machine learning model, may function to transfer each corpus of learned parameters (e.g., weights, biases, coefficients and/or the like) of the machine learning model during each distinct epoch of training to a subsequent epoch of training the machine learning model, for training with a distinct one of a plurality of mini-corpora of training data samples until each of the plurality of mini-corpora of training data samples may have been used in a distinct training epoch.

In one or more embodiments, S236 may function to identify when a training epoch may be completed using one mini corpora, collect a plurality of parameters (e.g., weights, biases, coefficients and/or the like) and transmit these as initial parameters for a subsequent phase/epoch of training using a subsequent mini corpora of training dataset, wherein, a subsequent mini corpora of training dataset may include a subsequent batch of majority class data set. In a preferred implementation, S236 may function to use a same minority class data set and a distinct batch of majority class data set in each epoch of training. In one variant implementation, S236 may function to use one or more distinct subsets of minority class data set in each epoch of training. Additionally, or alternatively, in another variant implementation, S236 may function to use one or more overlapping subsets of minority class data set in each epoch of training. Additionally, or alternatively, in another variant implementation, S236 may function to use one or more overlapping subsets of majority class data set in each epoch of training. It shall be recognized that S236 may function to use any combination of minority and majority class data sets in mini corpora of training data set.

In one or more embodiments, S236 may function to include a method for intelligently training a subject machine learning model, using transfer to transfer learning, by repeating a process of training in a current epoch with a current mini corpora of a training data set, transmitting values of learned parameters (e.g., weights, coefficients, biases and/or the like) to a subsequent epoch, training with a subsequent mini corpora of the training data set using the current values of learned parameters (e.g., weights, coefficients, biases and/or the like) as initial values, and then transmitting the values learned in a subsequent epoch of training to a next epoch of training until the entirety of the plurality of min corpora training data samples may have been used in the transfer-to-transfer learning-based training. In some implementations, a training process may use only a subset of a training data set.

In one or more embodiments, a number of epochs in the transfer-to-transfer learning-based training may be the same as a number of mini corpora within the plurality of mini corpora of training data samples.

In a preferred embodiment, S236 may function to train a machine learning model using a same set of hyperparameters in each epoch. Examples of algorithm hyperparameters may be learning rate, mini batch size etc.

In one or more embodiments, S236 may function to include training with emerging or new labeled minority class data. In one or more implementations, S236 may function to enable a machine learning model to transfer learn further and update learnable parameters of a CNN from a currently developed stage as new minority class data may become available, without having to train an entirely new machine learning model.

2.40 Deployment of Transfer-To-Transfer Trained Model

S240, which includes implementing a trained machine learning model, may function to implement a machine learning model trained using a transfer-to-transfer learning-based training method for computer aided detection (CAD) of one or more medical conditions.

In one or more embodiments, S240 may function to deploy a machine learning model that may have applications in medical imaging including, but not limited to, detecting a presence of a disease and/or diagnosing a specified type of disease from a given visual representation. For example, a computer-implemented system implementing a machine learning model may be deployed that may take images, in the form of chest radiographs, as inputs and may determine whether the input images represent lungs affected by a target disease (e.g., COVID-19, etc.).

In one or more embodiments, S240 may function to deploy a machine learning model that may produce a disease or illness score as an output, wherein, the disease score may represent a probability or likelihood that a given model input may be associated with a given classification or category of illness or disease. For example, a machine learning model may be deployed that may take image data, as input, in the form of chest radiographs, X-rays and/or other visual representations, and may generate a score between any suitable range, such as 0 and 1, wherein, proximity of the score to lower end of the range may represent a higher probability of input image belonging to one classification label (e.g., healthy lungs) and proximity of the score to higher end of the range may represent higher probability of input image belonging to a subsequent classification label (e.g., lungs affected by a target disease like COVID 19 and/or the like).

Additionally, or alternatively, S240 may function to deploy a machine learning model ad-hoc, as a current model may be re-trained using transfer-to-transfer learning as new batches of training data set may become available. In such embodiments, S240 may function to deploy a machine learning model at pre-determined fixed or variable intervals.

Additionally, or alternatively, S240 may function to enable a user to select or reject predictions made by a deployed machine learning model. For example, radiologists may manually review and/or determine whether or not they should accept results of the computer aided detection (CAD) for a target disease (e.g., COVID 19, etc.) Additionally, or alternatively, class activation maps may be generated along with CAD outputs for insights into most important spatial areas and/or for specific abnormalities, wherein, class activation maps determine which parts of the data (e.g., an image) contributed the most to a final output of the model.

The system and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processors and/or the controllers. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

Although omitted for conciseness, the preferred embodiments include every combination and permutation of the implementations of the systems and methods described herein.

As a person skilled in the art will recognize from the previous detailed description and from the figures and claims, modifications and changes can be made to the preferred embodiments of the invention without departing from the scope of this invention defined in the following claims.

What is claimed:

1. A machine learning-based method for detecting COVID-19 based on a transfer-to-transfer learning-optimized training of a machine learning algorithm using an initially imbalanced training data corpus, the method comprising:

evaluating an imbalanced training data corpus of training data samples, comprising at least a first subset of training data samples having a first classification label and a second subset of training data samples having a second classification label;

identifying that the first subset of training data samples includes a number of training data samples satisfying or exceeding a training corpus imbalance threshold, the first subset of training data samples having the number of training data samples greater than a number of training data samples within the second subset of training data samples;

reconfiguring the imbalanced training data corpus to a plurality of distinct class-balanced mini-corpora of training data samples, wherein the reconfiguring includes:
  (i) partitioning the imbalanced training data corpus into a plurality of mini-corpora of training data samples in which each distinct mini-corpus of the plurality of mini-corpora includes an entirety of the training data samples within the second subset of training data samples; and
  (ii) allocating an equal number of the training data samples of the first subset into each of the plurality of mini-corpora of training data samples; and transfer-to-transfer learning-based training a subject machine learning algorithm to a trained machine learning model based on implementing the transfer-to-transfer learning-based training using the plurality of distinct class-balanced mini-corpora, wherein in use, the trained machine learning model predicts a presence or a non-presence of COVID-19 based on image data.

2. The method according to claim 1, further comprising:
implementing an image segmentation of each distinct image data input to the trained machine learning model;
wherein the training machine learning model predicts the presence or the non-presence of COVID-19 based on the image data comprising one image segment of the distinct image data input.

3. The method according to claim 2, wherein the training data samples comprise a plurality of distinct human thoracic images, wherein the image segmentation includes:
partitioning each of the plurality of distinct human thoracic images to two or more distinct, non-overlapping parts.

4. The method according to claim 3, wherein
the plurality of distinct human thoracic images comprise a plurality of distinct chest radiographs of human lungs having COVID-19 and a plurality of distinct chest radiographs of human lung not having COVID-19.

5. The method according to claim 3, further comprising:
pre-processing the training data samples by normalizing each of the training data samples of the imbalanced training data corpus by adjusting a contrast between a plurality of distinct components within each of the plurality of distinct human thoracic images.

6. The method according to claim 1, wherein
the first subset of training data samples comprises a plurality of distinct non-COVID-19 image data samples.

7. The method according to claim 1, wherein
the second subset of training data samples comprises a plurality of distinct COVID-19 image data samples.

8. The method according to claim 1, wherein
the machine learning model comprises a convolution neural network.

9. The method according to claim 1, wherein
allocating the training data samples of the first subset into each of the plurality of mini-corpora of training data samples includes:
spreading the training data samples from the first subset as non-repetitive data samples among the plurality of mini-corpora of training data samples such that the training data samples within each of the plurality of mini-corpora of training data samples do not overlap.

10. The method according to claim 1, wherein
the transfer-to-transfer learning-based training includes:
transferring a corpus of learned parameters of a transferring machine learning model;
initializing the machine learning model based on the corpus of learned parameters.

11. The method according to claim 10, wherein
training the machine learning algorithm includes:
providing only a first one of the plurality of mini-corpora of training data samples as input training data examples to the machine learning algorithm during a first training phase.

12. The method according to claim 11, further comprising:
collecting a corpus of learned weights derived from training the machine learning model during the first training phase; and
transferring the corpus of learned weights to a new iteration of the machine learning algorithm.

13. The method according to claim 12, further comprising:
training the new iteration of the machine learning algorithm including:
providing only a second one of the plurality of mini-corpora of training data samples as input training data examples to the new iteration of the machine learning algorithm during a subsequent training phase.

14. The method according to claim 12, further comprising:
transferring each corpus of learned weights of the machine learning algorithm during each distinct training phase to a subsequent iteration of the machine learning algorithm for training with a distinct one of the plurality of mini-corpora of training data samples until each of the plurality of mini-corpora of training data samples has been using in a distinct training phase.

15. A method for training a machine learning algorithm for detecting COVID-19 based on transfer-to-transfer learning-based training, the method comprising:
evaluating an imbalanced training data corpus of training data samples, the imbalanced training data corpus comprising at least a first subset of training data samples with a first classification label and a second subset of training data samples with a second classification label;
wherein the first subset of training data samples having a number of training data samples greater than a number of training data samples than the second subset of training data samples;
partitioning the imbalanced training data corpus into a plurality of mini-corpora of training data samples having an equal number of training data samples from each of the first subset and the second subset of training data samples, wherein the partitioning includes:
(i) allocating a copy of all the training data samples of the second subset of training data samples into each of the plurality of mini-corpora;
(ii) allocating distinct subsets of the first subset of training data samples into each of the plurality of mini-corpora; and
training a machine learning algorithm to a trained machine learning model based on the plurality of mini-corpora, wherein, in use, the trained machine learning model predicts a presence or a non-presence of COVID-19 based on image data.

16. A machine learning-based Computer-Aided-Detection (CAD) system for detecting COVID-19 based on a transfer-to-transfer learning optimized training of a machine learning algorithm using an initially imbalanced training data corpus, the method comprising:
a machine learning-based Computer-Aided-Detection system implemented by one or more computers and that includes:
a training data reconfiguration module that:
evaluates an imbalanced training data corpus of training data samples, comprising at least a first subset of training data samples with a first classification label and a second subset of training data samples with a second classification label;
identifies that the first subset of training data samples includes a number of training data samples satisfying or exceeding a training corpus imbalance threshold, the first subset of training data samples having the number of training data samples greater than a number of training data samples within the second subset of training data samples;
configures the imbalanced training data corpus to a plurality of distinct class-balanced mini-corpora of training data samples, wherein the configuring includes:
(i) partitioning the imbalanced training data corpus into a plurality of mini-corpora of training data samples in which each distinct mini-corpus of the plurality of mini-corpora includes an entirety of the training data samples within the second subset of training data samples; and
(ii) allocating an equal number of the training data samples of the first subset into each of the plurality of mini-corpora of training data samples; and
a machine learning algorithm training module that:
trains a machine learning algorithm to a trained machine learning model based on the plurality of mini-corpora, wherein in use the trained machine learning model predicts a presence or a non-presence of COVID-19 based on image data.

17. The system according to claim 16, the machine learning-based CAD system further comprising:
an image segmentation module that:
segments of each of the training data samples of the imbalanced training data corpus, wherein the training data samples comprise a plurality of distinct human thoracic images, wherein the image segmentation includes:
partitions each of the plurality of distinct human thoracic images to two or more distinct, non-overlapping parts.

* * * * *